(12) United States Patent
Campbell

(10) Patent No.: US 6,534,511 B1
(45) Date of Patent: Mar. 18, 2003

(54) BICYCLIC HETEROCYCLIC COMPOUNDS FOR THE TREATMENT OF IMPOTENCE

(75) Inventor: Simon Fraser Campbell, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/542,489

(22) Filed: Apr. 3, 2000

Related U.S. Application Data

(62) Division of application No. 08/836,671, filed as application No. PCT/EP95/04065 on Oct. 16, 1995, now Pat. No. 6,100,270.

(30) Foreign Application Priority Data

Nov. 26, 1994 (GB) .............................................. 9423911

(51) Int. Cl.$^7$ ..................... A61K 31/505; A61K 31/535
(52) U.S. Cl. ...................................... 514/258; 514/234
(58) Field of Search ................................. 514/258, 234

(56) References Cited

FOREIGN PATENT DOCUMENTS

| EP | 0463756 | 1/1992 | ......... C07D/487/04 |
|---|---|---|---|
| EP | 0526004 | 2/1993 | ......... C07D/487/04 |
| EP | 0535924 | 4/1993 | ......... C07D/401/12 |
| FR | 2547501 | 12/1984 | .......... A61K/17/00 |
| JP | 3044324 | 2/1991 | .......... A61K/31/52 |
| WO | 8910123 | 11/1989 | .......... A61K/31/35 |
| WO | WO 9306104 | 4/1993 | ......... C07D/487/04 |
| WO | WO 9307149 | 4/1993 | ......... C07D/487/04 |
| WO | WO 9312095 | 6/1993 | ......... C07D/239/91 |
| WO | WO 9400453 | 1/1994 | ......... C07D/473/30 |
| WO | WO 9405661 | 3/1994 | ......... C07D/471/04 |
| WO | WO 9428902 | 12/1994 | .......... A61K/31/505 |
| WO | WO 9429277 | 12/1994 | ......... C07D/233/38 |

OTHER PUBLICATIONS

ABPI Data Sheet Compendium, 1990–1991; pp. 740–742.
Rote Liste 1992.
Medicinal and Poisonous Plants in Southwest Africa, Ebrhard von Koenen, 1979.
Pharmacological Expert Opinion on the Use of cGMP Inhibitors for the Oral Treatment of Erectile Dysfunction in Men, Professor J. C. Frolich, Exhibit 2, 1998.
Journal of Japanese Society of Urology, Oct. 1992, vol. 83, No. 1, pp. 1655–1661, Yasuo Kawanishi, et al.
Optimizing Therapy with Methylxanthines, Ekkehard Haen, et al., Aug. 1989, C1435–C1440.
Hagers Handbuch Der Pharmazeutischen Praxis, begonnen Von W. Kern, et al., 1971, p. 675–676.
Br. J. Pharmacol. 1992, 106, 1028–1034, Jacob de Boer, et al.
The Journal of Urology, vol. 149, Apr. 1993, No. 4, AUA Eighty–Eighth Annual Meeting May 15–20, Abstract 285.
Physician's Desk Reference, 1992, 46th Edition, pp. 1099–1100.
Trends in Pharmacological Sciences, Jan. 1991, vol. 12, No. 1, C. David Nicholson, et al., pp. 150–155.
CNN—Viagra?, Jun. 19, 1998.
Pharmac. Ther. vol. 51, pp. 13–33, 1991, W. Joseph Thompson.
Aronson, et al., J. Urol. 147 Supp 45A, 1992, No. 967.
International Journal of Impotence Research, vol. 6, No. 1, Mar. 1994, A. W. Zorgniotti, et al, pp. 33–36.
Drug Therapy, Aug. 1989, Treating Erectile Dysfuntion, I.J. Fishman, pp. 102–111.
Molecular Pharmacology, vol. 36, No. 5, Nov. 1989, Peter G. Gillespie, and Joseph A. Beavo, pp. 773–781.
J. Mol. Cell Cardiol, 1980, 12/10 (939–954), Abstract.
Postgraduate Medicine, vol. 93, No. 3, Management of Impotence, John E. Morley, pp. 65–72 1993.
Biochemical Pharmacology, vol. 46, No. 5, pp. 833–839, 1993, T. Saeki et al.
Tohoku J. Exp. Med., 1991, 165, Yoshlastu Takahashi, et al, pp. 49–58.
Br. J. Dis. Chest, 1986, 80, J. Reiser, et al, pp. 157–163.
Journal of Medicine, vol. 10, No. 6, 1979, J. L. Ambrus, et al, pp. 445–456.
Br. J. Pharmacology., 1993, 108, 562–568, J. Cortijo, et al.
Journal of Ethnopharmacology, 12, 1984, 36–74, Hans–Joechim Arnold, et al.
Journal of Pharm. & Exper. Therapeutics, 1989, vol. 251, E. G. McMahon, et al, pp. 1000–1005.
British Journal of Diseases of the Chest, Robin M. Rudd, et al, 1988, 77, pp. 78–86.
The Journal of Urology, vol. 145, No. 4, 1991, AUA Eighty–six Annual Meeting Jun. 2–6, 1991, p. 341A, Abstract 586.
Martindale The Extra Pharmacopoeia, 29th Ed., 1989, p. 1423, heading 14026–m.
Archives of Pharmacology, W. R. Kukovetz, Evidence for Cyclic GMP–Mediated Relaxant Effects of Nitro–Compounds in Coronary Smooth Muscle 1979.
Journal of the American Geriatrics Society, vol. 41, No. 4, 1993, Stanley G. Korenman, et al., p. 363–366.
Angiology—Journal of Vascular Diseases, 1991, pp. 418–420 Kent S. Allenby, et al.
Clin. Res., vol. 36(1), 123(A), Korenmann SG, Treatment of Vasculogema Sexual Dysfunction with pentoxyfylline 1993.

(List continued on next page.)

Primary Examiner—Rebecca Cook
(74) Attorney, Agent, or Firm—Peter C. Richardson; Gregg C. Benson; James T. Jones

(57) ABSTRACT

The use of certain 6-arylpyrazolo[3,4-d]pyrimidin-4-ones, 2 arylquinazolin-4-ones, 2-arylpurin-6-ones and 2-arylpyrido [3,2-d]pyrimidin-4-ones, or a pharmaceutically acceptable salt thereof, or a pharmaceutical composition containing either entity, for the manufacture of a medicament for the curative or prophylactic treatment of erectile dysfunction in a male animal, including man; a pharmaceutical composition for said treatment; and a method of said treatment of said animal with said pharmaceutical composition or with said either entity.

3 Claims, No Drawings

OTHER PUBLICATIONS

American Physiological Society, Joseph A. Beavo, Cyclic Nucleotide Phosphodiesterases: Functional Implications of Multiple Isoforms, pp. 725–748 1990.

Pharmacological Activities of the Main Metabolite of Flavoxate 3–Methylflavone–8–carboxylic Acid, Arzenmittel-–Forschung, P. Cazzulani, et al, pp. 379–382 1988.

Trends in Pharmacological Sciences, vol. 11, No. 4, 1990, Joseph A. Beavo, et al. pp. 19–27.

ABPI compendium—Trental 400 summary sheet 1990.

Taher et al., Int. J. Impotence Res., 1992, vol. 4, Suppl 2, pp. 11.

Neurol Urodyn, vol. 13, No. 1, 1994, 71–79.

Am J. Physiol. Heart circ. Physiol, vol. 264, No. 2, 1993.

Rajfer et al., New Eng. Jrnl. Med. 326(2), 90–94, 1992.

Bowman et al., Br. J. Pharm. 81, 665–674, 1984.

Bush et al. J. Urol. 147, 1650–1655, 1992.

Kenneth J.Murray, D. N. &. P., 6(3), 150–156, 1993.

BICYCLIC HETEROCYCLIC COMPOUNDS FOR THE TREATMENT OF IMPOTENCE

This is a division of application Ser. No. 08/836,671, filed on May 22, 1997, now U.S. Pat. No. 6,100,270 entitled Bicyclic Heterocyclic Compounds For The Treatment of Impotence which is the national stage under 35 U.S.C. §371(c) of International Patent Application No. PCT/EP95/04065, filed Internationally on Oct. 16, 1995.

This invention relates to the use of certain pyrazolo[4,3-d]pyrimidin-7-ones, pyrazolo[3,4-d]pyrimidin-4-ones, quinazolin-4-ones, purin-6-ones and pyrido[3,2-d]pyrimidin-4-ones for the treatment of impotence.

Impotence can be defined literally as a lack of power, in the male, to copulate and may involve an inability to achieve penile erection or ejaculation, or both. More specifically, erectile impotence or dysfunction may be defined as an inability to obtain or sustain an erection adequate for intercourse. Its prevalence is claimed to be between 2 and 7% of the human male population, increasing with age, up to 50 years, and between 18 and 75% between 55 and 80 years of age. In the USA alone, for example, it has been estimated that there are up to 10 million impotent males, with the majority suffering from problems of organic rather than of psychogenic origin.

Reports of well-controlled clinical trials in man are few and the efficacy of orally administered drugs is low. Although many different drugs have been shown to induce penile erection, they are only effective after direct injection into the penis, e.g. intraurethrally or intracavernosally (i.c.), and are not approved for erectile dysfunction. Current medical treatment is based on the i.c injection of vasoactive substances and good results have been claimed with phenoxybenzamine, phentolamine, papaverine and prostaglandin $E_1$, either alone or in combination; however, pain, priapism and fibrosis of the penis are associated with the i.c. administration of some of these agents. Potassium channel openers (KCO) and vasoactive intestinal polypeptide (VIP) have also been shown to be active i.c., but cost and stability issues could limit development of the latter. An alternative to the i.c. route is the use of glyceryl trinitrate (GTN) patches applied to the penis, which has been shown to be effective but produces side-effects in both patient and partner.

As a general alternative to pharmacological intervention, a variety of penile prostheses has been used to assist achievement of an erection. The short term success rate is good, but problems with infection and ischaemia, especially in diabetic men, make this type of treatment a final option rather than first-line therapy.

The compounds of the invention are potent inhibitors of cyclic guanosine 3',5'-monophosphate phosphodiesterases (cGMP PDES) in contrast to their inhibition of cyclic adenosine 3',5'-monophosphate phosphodiesterases (cAMP PDEs). This selective enzyme inhibition leads to elevated cGMP levels which, in turn, provides the basis for the utilities already disclosed for the said compounds in WO-A-93/06104, WO-A-93/07149, WO-A-93/12095, WO-A-94/00453 and WO-A-94/05661 respectively, namely in the treatment of stable, unstable and variant (Prinzmetal) angina, hypertension, pulmonary hypertension, congestive heart failure, atherosclerosis, conditions of reduced blood vessel patency e.g. post-percutaneous transluminal coronary angioplasty (post-PTCA), peripheral vascular disease, stroke, bronchitis, allergic asthma, chronic asthma, allergic rhinitis, glaucoma, and diseases characterised by disorders of gut motility, e.g. irritable bowel syndrome (IBS).

Unexpectedly, it has now been found that these disclosed compounds are useful in the treatment of erectile dysfunction. Furthermore the compounds may be administered orally, thereby obviating the disadvantages associated with i.c. administration. Thus the present invention concerns the use of a compound of formula (I):

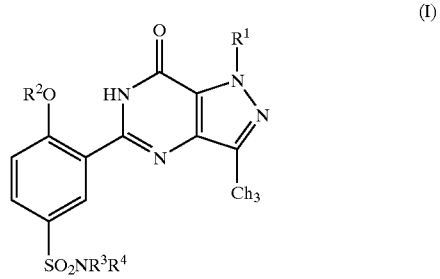

(I)

wherein $R^1$ is methyl or ethyl;

$R^2$ is ethyl or n-propyl; and $R^3$ and $R^4$ are each independently H, or $C_1$–$C_6$ alkyl optionally substituted with $C_5$–$C_7$ cycloalkyl or with morpholino;

a compound of formula (II):

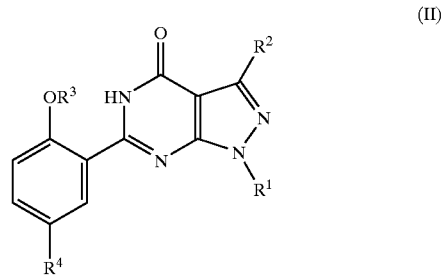

(II)

wherein $R^1$ is $C_1$–$C_6$ alkyl;

$R^2$ is H; methyl or ethyl;

$R^3$ is $C_2$–$C_4$ alkyl;

$R^4$ is H; $C_1$–$C_4$ alkyl optionally substituted with $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; $SO_2NR^5R^6$; $CONR^5R^6$; $CO_2R^7$ or halo; $R^5$ and $R^6$ are each independently H or $C_1$–$C_4$ alkyl; or, together with the nitrogen atom to which they are attached, form a pyrrolidino, piperidino, morpholino, 4-($NR^8$)-1-piperazinyl or 1-imidazolyl group wherein said group is optionally substituted with one or two $C_1$–$C_4$ alkyl groups;

$R^7$ is H or $C_1$–$C_4$ alkyl; and $R^8$ is H; $C_1$–$C_3$ alkyl or (hydroxy) $C_2$–$C_3$ alkyl;

a compound of formula (III):

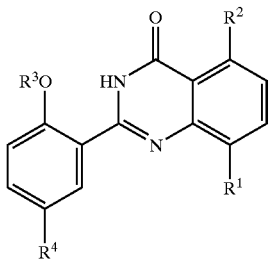

(III)

wherein

R¹ is H; $C_1$–$C_4$ alkyl; $C_1$–$C_4$ alkoxy or $CONR^5R^6$;

R² is H or $C_1$–$C_4$ alkyl;

R³ is $C_2$–$C_4$ alkyl;

R⁴ is H; $C_2$–$C_4$ alkanoyl optionally substituted with $NR^7R^8$; (hydroxy)$C_2$–$C_4$ alkyl optionally substituted with $NR^7R^8$; $CH=CHCO_2R^9$; $CH=CHCONR^7R^8$; $CH_2CH_2CO_2R^9$; $CH_2CH_2CONR^7R^8$; $SO_2NR^7R^8$; $SO_2NH(CH_2)_nNR^7R^8$ or imidazolyl;

R⁵ and R⁶ are each independently H or $C_1$–$C_4$ alkyl;

R⁷ and R⁸ are each independently H or $C_1$–$C_4$ alkyl; or, together with the nitrogen atom to which they are attached, form a pyrrolidino, piperidino, morpholino or 4-($NR^{10}$)-1-piperazinyl group wherein any of said groups is optionally substituted with $CONR^5R^6$;

R⁹ is H or $C_1$–$C_4$ alkyl;

R¹⁰ is H; $C_1$–$C_3$ alkyl or (hydroxy)$C_2$–$C_3$ alkyl; and n is 2, 3 or 4;

with the proviso that R⁴ is not H when R¹ is H, $C_1$–$C_4$ alkyl or $C_1$–$C_4$ alkoxy;

a compound of formula (IV):

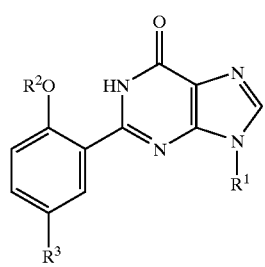

(IV)

wherein

R¹ is $C_1$–$C_4$ alkyl;

R² is $C_2$–$C_4$ alkyl;

R³ is H or $SO_2NR^4R^5$;

R⁴ and R⁵ together with the nitrogen atom to which they are attached form a pyrrolidino, piperidino, morpholino or 4-($NR^6$)-1-piperazinyl group; and R⁶ is H or $C_1$–$C_3$ alkyl;

or a compound of formula (V):

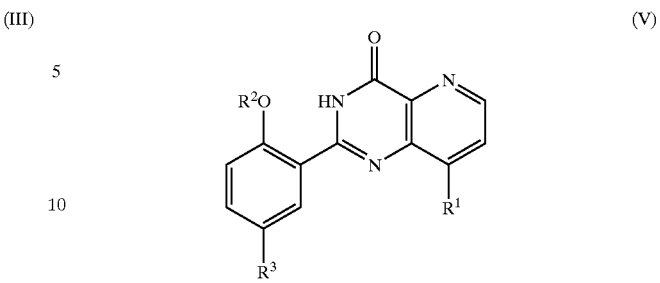

(V)

wherein

R¹ is H; $C_1$–$C_4$ alkyl; CN or $CONR^4R^5$;

R² is $C_2$–$C_4$ alkyl;

R³ is $SO_2NR^6R^7$; $NO_2$; $NH_2$; $NHCOR^8$; $NHSO_2R^8$ or $N(SO_2R^8)_2$;

R⁴ and R⁵ are each independently selected from H and $C_1$–$C_4$ alkyl;

R⁶ and R⁷ are each independently selected from H and $C_1$–$C_4$ alkyl optionally substituted with $CO_2R^9$, OH, pyridyl, 5-isoxazolin-3-onyl, morpholino or 1-imidazolidin-2-onyl; or, together with the nitrogen atom to which they are attached, form a pyrrolidino, piperidino, morpholino, 1-pyrazolyl or 4-($NR^{10}$)-1-piperazinyl group wherein any of said groups may optionally be substituted with one or two substituents selected from $C_1$–$C_4$ alkyl, $CO_2R^9$, $NH_2$ and OH;

R⁸ is $C_1$–$C_4$ alkyl or pyridyl;

R⁹ is H or $C_1$–$C_4$ alkyl; and

R¹⁰ is H; $C_1$–$C_4$ alkyl or (hydroxy)$C_2$–$C_3$ alkyl;

or a pharmaceutically acceptable salt thereof, or a pharmaceutical composition containing either entity, for the manufacture of a medicament for the curative or prophylactic treatment of erectile dysfunction in a male animal, including man.

In the above definition, unless otherwise indicated, alkyl and alkoxy groups having three or more carbon atoms, and alkenyl and alkanoyl groups having four carbon atoms, may be straight chain or branched chain. Halo means fluoro, chloro, bromo or iodo.

The compounds of the invention may contain one or more asymmetric centres and thus they can exist as enantiomers or diastereoisomers. Furthermore, certain compounds of formulae (II) and (III) which contain alkenyl groups may exist as cis-isomers or trans-isomers. In each instance, the invention includes both mixtures and separate individual isomers.

The compounds of the invention may also exist in tautomeric forms and the invention includes both mixtures and separate individual tautomers.

The pharmaceutically acceptable salts of the compounds of the invention which contain a basic centre are, for example, non-toxic acid addition salts formed with inorganic acids such as hydrochloric, hydrobromic, sulphuric and phosphoric acid, with organo-carboxylic acids, or with organo-sulphonic acids. The compounds of the invention can also provide pharmaceutically acceptable metal salts, in particular non-toxic alkali metal salts, with bases. Examples include the sodium and potassium salts. For a review on suitable pharmaceutical salts, see J. Pharm. Sci., 1977, 66, 1.

A preferred group of compounds is that of formula (I) wherein R³ is H; methyl or ethyl; R⁴ is $C_1$–$C_6$ alkyl optionally substituted with cyclohexyl or with morpholino; and R¹ and R² are as previously defined for formula (I); of formula (II) wherein $R^1$ is n-propyl; $R^2$ is H or methyl; $R^3$ is ethyl or n-propyl; $R^4$ is H; ethyl substituted with $CONR^5R^6$ or $CO_2R^7$; vinyl substituted with $CONR^5R^6$ or $CO_2R^7$; acetyl substituted with $NR^5R^6$; $SO_2NR^5R^6$; $CONR^5R^6$; $CO_2R^7$ or bromo; $R^5$ and $R^6$ together with the nitrogen atom to which they are attached form a morpholino, 4-($NR^8$)-1-piperazinyl or 2,4-dimethyl-1-midazolyl group; $R^7$ is H or t-butyl; and $R^8$ is methyl or 2-hydroxyethyl; of formula (III) wherein $R^1$ is H; methyl; methoxy or $CONR^5R^6$; $R^2$ is H or methyl; $R^3$ is ethyl or n-propyl; $R^4$ is H; acetyl optionally substituted with $NR^7R^8$; hydroxyethyl substituted with $NR^7R^8$; $CH=CHCO_2R^9$; $CH=CHCONR^7R^8$; $CH_2CH_2CO_2R^9$; $SO_2NR^7R^8$; $SO_2NH(CH_2)_3NR^7R^8$ or 1-imidazolyl; $R^5$ and $R^6$ are each independently H or ethyl; $R^7$ and $R^8$ together with the nitrogen atom to which they are attached form a piperidino, 4-carbamoylpiperidino, morpholino or 4-($NR^{10}$)-1-piperazinyl group; $R^9$ is H or t-butyl; and $R^{10}$ is H; methyl or 2-hydroxyethyl; with the proviso that $R^4$ is not H when $R^1$ is H, methyl or methoxy; of formula (IV) wherein $R^1$ and $R^2$ are each independently ethyl or n-propyl; $R^4$ and $R^5$ together with the nitrogen atom to which they are attached form a 4-($NR^6$)-1-piperazinyl group; and $R^3$ and $R^4$ are as previously defined for formula (IV); and of formula (V) wherein $R^1$ is H; n-propyl; CN or $CONH_2$; $R^2$ is ethyl; $R^3$ is $SO_2NR^6R^7$; $NO_2$; $NH_2$; $NHCOCH(CH_3)_2$; $NHSO_2CH(CH_3)_2$; $NHSO_2$(3-pyridyl) or $N[SO_2$(3-pyridyl)$]_2$ ; $R^6$ is H; methyl or 2-hydroxyethyl; $R^7$ is methyl optionally substituted with 2-pyridyl or 5-isoxazolin-3-onyl; or ethyl 2-substituted with OH, $CO_2CH_2CH_3$, morpholino or 1-imidazolidin-2-onyl; or $R^6$ and $R^7$ together with the nitrogen atom to which they are attached form a (4-$CO_2R^9$)piperidino, 5-amino-3-hydroxy-1pyrazolyl or 4-($NR^{10}$)-1piperazinyl group; $R^9$ is H or ethyl; and $R^{10}$ is H; methyl or 2-hydroxyethyl.

A particularly preferred group of compounds is that of formula (III) wherein $R^1$ is methyl; $CONH_2$ or $CONECH_2CH_3$; $R^2$ is H; $R^3$ is ethyl or n-propyl; $R^4$ is H; acetyl; 1-hydroxy-2-($NR^7R^8$)ethyl; $CH=CHCO_2C(CH_3)_3$; $CH=CHCONR^7R^8$; $SO_2NR^7R^8$ or 1-imidazolyl; $R^7$ and $R^8$ together with the nitrogen atom to which they are attached form a 4-($NR^{10}$)-1piperazinyl group; and $R^{10}$ is methyl or 2-hydroxyethyl; with the proviso that $R^4$ is not H when $R^1$ is methyl; of formula (IV) wherein $R^1$ is n-propyl; $R^2$ is ethyl; and $R^3$ is 1-piperazinylsulphonyl or 4-methyl-1-piperazinylsulphonyl; and of formula (V) wherein $R^1$ is n-propyl or CN; $R^2$ is ethyl; $R^3$ is $SO_2NR^6R^7$; $NHSO_2CH(CH_3)_2$; $NHSO_2$(3-pyridyl) or $N[SO_2$(3-pyridyl)$]_2$; $R^6$ is H or methyl; $R^7$ is methyl; or ethyl 2-substituted with $CO_2CH_2CH_3$; morpholino or 1-imidazolidin-2-onyl; or $R^6$ and $R^7$ together with the nitrogen atom to which they are attached form a (4-$CO_2R^9$)-piperidino or 4-($NR^{10}$)-1piperazinyl group; $R^9$ is H or ethyl; and $R^{10}$ is H; methyl or 2-hydroxyethyl.

Especially preferred individual compounds of the invention include:

1-ethyl-5-[5-(n-hexylsulphamoyl)-2-n-propoxyphenyl]-3-methyl-1,6-dihydro-7H-pyrazolo[4,3-d]pyrimidin-7-one;

1-ethyl-5-(5-diethylsulphamoyl-2-n-propoxyphenyl)-3-methyl-1,6-dihydro-7H-pyrazolo[4,3-d]-pyrimidin-7-one;

5-[5-(N-cyclohexylmethyl-N-methylsulphamoyl)-2-n-propoxyphenyl]-1-ethyl-3-methyl-1,6-dihydro-7H-pyrazolo[4,3-d]pyrimidin-7-one;

6-(5-bromo-2-n-propoxyphenyl)-3-methyl-1n-propyl-1,5-dihydro-4H-pyrazolo[3,4-d]pyrimidin-4-one;

3-methyl-6-(5-morpholinosulphonyl-2-n-propoxyphenyl)-1n-propyl-1,5-dihydro-4H-pyrazolo[3,4-d]pyrimidin-4-one;

6-[5-(2-carboxyvinyl)-2-n-propoxyphenyl]-3-methyl-1-n-propyl-1,5-dihydro-4H-pyrazolo[3,4-d]pyrimidin-4-one;

6-[5-(2-t-butoxycarbonylvinyl)-2-n-propoxyphenyl]-3-methyl-1n-propyl-1,5-dihydro-4H-pyrazolo[3,4-d]pyrimidin-4-one;

3-methyl-6-[5-(2-morpholinocarbonylvinyl)-2-n-propoxyphenyl]-1-n-propyl-1,5-dihydro-4H-pyazolo[3,4-d]pyrimidin-4-one;

3-methyl-6-[5-(2-morpholinocarbonylethyl)-2-n-propoxyphenyl]-1-n-propyl-1,5-dihydro-4H-pyrazolo[3,4-d]pyrimidin-4-one;

2-{2-ethoxy-5-[4-(2-hydroxyethyl)-1-piperazinylsulphonyl]phenyl}-8-methylquinazolin-4-(3H)-one;

2-{5-[4-(2-hydroxyethyl)-1-piperazinylsulphonyl]-2-n-propoxyphenyl}-8-methylquinazolin-4(3H)-one;

8-methyl-2-{5-[2-(4-methyl-1-piperazinylcarbonyl)-ethenyl]-2-n-propoxyphenyl}quinazolin-4(3H)-one;

8-carbamoyl-2-{2-ethoxy-5-[4-(2-hydroxyethyl)-1-piperazinylsulphonyl]phenyl}quinazolin-4(3H)-one;

8-ethylcarbamoyl-2-(2-n-propoxyphenyl)quinazolin-4(3H)-one;

2-[2-ethoxy-5-(4-ethoxycarbonylpiperidinosulphony)phenyl]-8-n-propylpyrido[3,2-d]pyrimidin-4(3H)-one;

2-[5-(4-carboxypiperidinosulphonyl)-2-ethoxyphenyl]-8-n-propylpyrido[3,2-d]pyrimidin-4(3H)-one;

2-{2-ethoxy-5-[4-(2-hydroxyethyl)-1-piperazinylsulphonyl]phenyl}-8-n-propylpyrido[3,2-d]pyrimidin-4(3H)-one; and 2-{2-ethoxy-5-[(bis-3-pyridylsulphonyl)amino]-phenyl}-8-n-propylpyrido[3,2-d]pyrimidin-4(3H)-one.

The compounds of formulae (I), (II), (III), (IV) and (V) and their pharmaceutically acceptable salts, processes for the preparation thereof, in vitro test methods for determining the cGMP PDE and cAMP PDE inhibitory activities thereof, pharmaceutical compositions thereof and routes of administration for human use, are described in WO-A-93/06104, WO-A-93/07149, WO-A-93/12095, WO-A-94/00453 and WO-A-94/05661 respectively, which are incorporated herein by reference.

A preliminary investigation was carried out with a view to isolating and characterising the cyclic nucleotide PDEs of human corpus cavernosum, relaxation of which leads to penile erection. Studies of substrate specificity, response to activators and inhibitor sensitivity, have demonstrated that human corpus cavernosum contains three distinct PDE enzymes.

Methods

Fresh frozen human penis was obtained from IIAM (Pennsylvania). Tissue was thawed at room temperature, the corpus cavernosum was dissected from the penis to yield approximately 2–4 g of tissue and the following isolation protocol was followed. Tissue was coarsely chopped in ice-cold isotonic buffer (35 ml) containing 250 mM sucrose, 1 mM EDTA, 0.5 mM PMSF and 20 mM HEPES, pH 7.2, and the mixture subjected to brief (1 min.) treatment with a Silversen mixer/emulsifier. Homogenates were prepared using homogeniser tubes with teflon pestles and soluble fraction was prepared by centrifugation at 100,000×g for 60 min. at 4° C. 10 ml of high speed supernatant was applied to a Pharmacia Mono Q anion exchange column (1 ml bed volume) equilibrated with buffer containing 1 mM EDTA, 0.5 mM PMSF and 20 mM HEPES, pH 7.2 (chromatography buffer). The column was then washed with 5 bed volumes of chromatography buffer, after which PDEs were eluted using a continuous gradient of 0–500 mM NaCl (total volume 35 ml) and 1 ml fractions collected.

Column fractions were assayed for PDE activity using 500 nM cGMP or 500 nM cAMP as substrate. cAMP PDE activity was also determined in the presence of 1 μM unlabelled cGMP and the PDE activity of selected fractions was determined in the presence of 10 mM $CaCl_2$ and 10 units/ml bovine brain calmodulin. Appropriate fractions were pooled and stored at 4° C. during the course of the study.

Inhibition studies were performed using a substrate concentration of 500 nM throughout. All inhibitors were dissolved in DMSO and concentration-response curves were constructed over the range $3\times10^{-10}$ to $1\times10^{-4}$M in half log increments. $IC_{50}$ values were calculated using the sigmoidal curve fitting algorithm of biostat.

Results

Human corpus cavernosum soluble PDEs were separated into three distinct fractions of activity. The first, fraction I, (designated by order of elution) represents the major PDE present and is highly selective for cGMP as substrate. This fraction was found to be insensitive to stimulation by calcium/calmodulin and was classified as $PDE_V$. Fraction II hydrolyses cGMP and cAMP, with the latter activity being stimulated in the presence of cGMP, and is classified as $PDE_{II}$, whilst fraction III is cAMP selective and this activity is inhibited in the presence of cGMP, consistent with $PDE_{III}$ activity.

In order to further characterise the PDE isoenzymes present in the tissue, studies were performed using a variety of inhibitors. Inhibitor studies with fractions I and II were performed using cGMP as substrate, whilst fraction III studies utilised cAMP. These studies confirmed that fraction I corresponds to $PDE_V$, whilst fraction III was clearly identified as $PDEX_{III}$; fraction II ($PDE_{II}$) was relatively insensitive to all the inhibitors tested.

In summary, the above investigation identified three PDE isoenzymes in human corpus cavernosum tissue. The predominant PDE is the cGMP-specific $PDE_V$, whilst cGMP-stimulated cAMP $PDE_{II}$ and cGMP-inhibited cAMP $PDE_{III}$ are also present.

Certain compounds of the invention have been tested in vitro and found to be potent and selective inhibitors of the cGMP-specific $PDE_V$. Thus relaxation of the corpus cavernosum tissue and consequent penile erection is presumably mediated by elevation of cGMP levels in the said tissue, by virtue of the PDE inhibitory profile of the compounds of the invention.

Although the compounds of the invention are envisaged primarily for the treatment of erectile; dysfunction or male sexual dysfunction, they may also be useful for the treatment of female sexual dysfunction, including orgasmic dysfunction related to clitoral disturbances, and of premature labour and dysmenorrhea.

Generally, in man, oral administration of the compounds of the invention is the preferred route, being the most convenient and avoiding the disadvantages associated with i.c. administration. A preferred dosing regimen for a typical man is 5 to 75 mg of compound three times daily. In circumstances where the recipient suffers from a swallowing disorder or from impairment of drug absorption after oral administration, the drug may be administered parenterally, e.g. sublingually or buccally.

For veterinary use, a compound of the invention or a non-toxic salt thereof is administered as a suitably acceptable formulation in accordance with normal veterinary practice and the veterinary surgeon will determine the dosing regimen and route of administration which will be most appropriate for a particular male animal.

Thus the invention includes a pharmaceutical composition for the curative or prophylactic treatment of erectile dysfunction in a male animal, including man, comprising a compound of formula (I), (II), (III), (IV) or (V), or a pharmaceutically acceptable salt thereof, together with a pharmaceutically acceptable diluent or carrier.

There is further provided a process for the preparation of a pharmaceutical composition for the curative or prophylactic treatment of erectile dysfunction in a male animal, including man, comprising formulating a compound of formula (I), (II), (III), (IV) or (V), or a pharmaceutically acceptable salt thereof, with a pharmaceutically acceptable diluent or carrier.

The invention also provides a method of treating a male animal, including man, to cure or prevent erectile dysfunction which comprises treating said male animal with an effective amount of a compound of formula (I), (II), (III), (IV) or.(V), or a pharmaceutically acceptable salt thereof, or a pharmaceutical composition containing either entity.

What is claimed is:

1. A method of treating male erectile dysfunction, comprising administering, to a male human in need of said treatment an effective amount of a compound of formula (II):

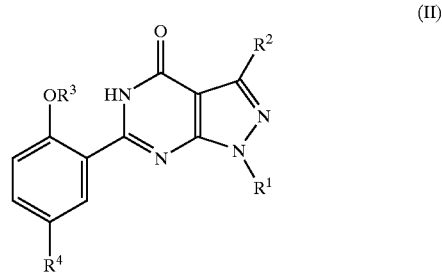

(II)

wherein
  $R^1$ is $C_1$–$C_6$ alkyl;
  $R^2$ is H; methyl or ethyl;
  $R^3$ is $C_2$–$C_4$ alkyl;
  $R^4$ is H; $C_1$–$C_4$ alkyl optionally substituted with $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; $SO_2NR^5R^6$; $CONR^5R^6$; $CO_2R^7$ or halo;
  $R^5$ and $R^6$ are each independently H or $C_1$–$C_4$ alkyl; or, together with the nitrogen atom to which they are attached, form a pyrrolidino, piperidino, morpholino, 4-($NR^8$)-1-piperazinyl or 1-imidazolyl group wherein said group is optionally substituted with one or two $C_1$–$C_4$ alkyl groups;
  $R^7$ is H or $C_1$–$C_4$ alkyl; and
  $R^8$ is H; $C_1$–$C_3$ alkyl or (hydroxy)$C_2$–$C_3$ alkyl;
or a pharmaceutically acceptable salt thereof, or a pharmaceutical composition containing either entity.

2. The method according to claim 1 wherein: in a compound of formula (II) $R^1$ is n-propyl; $R^2$ is H or methyl; $R^3$ is ethyl or n-propyl; $R^4$ is H; ethyl substituted with $CONR^5R^6$ or $CO_2R^7$; vinyl substituted with $CONR^5R^6$ or $CO_2R^7$; acetyl substituted with $NR^5R^6$; $SO_2NR^5R^6$; $CONR^5R^6$; $CO_2R^7$ or bromo; $R^5$ and $R^6$ together with the nitrogen atom to which they are attached form a morpholino, 4-($NR^8$)-1-piperazinyl or 2,4-dimethyl-1-imidazolyl group; $R^7$ is H or t-butyl; and $R^8$ is methyl or 2-hydroxyethyl.

3. The method according to claim 2 wherein the compound of formula (II) is selected from:
  6-(5-bromo-2-n-propoxyphenyl)-3-methyl-1-n-propyl-1,5-dihydro-4H-pyrazolo[3,4-d]pyrimidin-4-one;

3-methyl-6-(5-morpholinosulphonyl-2-n-propoxyphenyl)-1n-propyl-1,5-dihydro-4H-pyrazolo[3,4-d]pyrimidin-4-one;

6-[5-(2-carboxyvinyl)-2-n-propoxyphenyl]-3-methyl-1-n-propyl-1,5-dihydro-4H-pyrazolo[3,4-d]pyrimidin-4-one;

6-[5-(2-t-butoxycarbonylvinyl)-2-n-propoxyphenyl]-3-methyl-1-n-propyl-1,5-dihydro-4H-pyrazolo[3,4-d]pyrimidin-4-one;

3-methyl-6-[5-(2-morpholinacarbonylvinyl)-2-n-propoxyphenyl]-1-n-propyl-1,5-dihydro-4H-pyrazolo[3,4-d]pyrimidin-4-one; and 3-methyl-6-[5-(2-morpholinocarbonylethyl)-2-n-propoxyphenyl]-1-n-propyl-1,5-dihydro-4H-pyrazolo[3,4-d]pyrimidin-4-one.

* * * * *